United States Patent [19]

Uwajima et al.

[11] Patent Number: 4,670,389

[45] Date of Patent: Jun. 2, 1987

[54] PROCESS FOR PRODUCING N-ACETYLNEURAMINATE LYASE

[75] Inventors: Takayuki Uwajima; Kazuo Aisaka, both of Machida, Japan

[73] Assignee: Kyowa Hakko Kogyo Co., Ltd., Tokyo, Japan

[21] Appl. No.: 743,802

[22] Filed: Jun. 12, 1985

[30] Foreign Application Priority Data

Jun. 14, 1984 [JP] Japan ................... 59-122818

[51] Int. Cl.$^4$ ............ C12N 15/00; C12N 9/88; C12N 1/20; C12R 1/19

[52] U.S. Cl. ............... 435/172.3; 435/232; 435/253; 435/849

[58] Field of Search ........ 435/232, 172.3, 253, 435/849

[56] References Cited

U.S. PATENT DOCUMENTS 4,362,817 12/1982 Reusser .................. 435/172.3
4,469,791 9/1984 Colson et al. ............. 435/253

FOREIGN PATENT DOCUMENTS 55-50890 4/1980 Japan ..................... 435/232

OTHER PUBLICATIONS

Saito et al, Biochimica et Biophysica Acta, vol. 72, (1963), pp. 619–629.
Patent Abstracts of Japan, unexamined applications, section C, vol. 4, No. 85, p. 149, Jun. 18, 1980, (Kokai No. 55-50890).
Patent Abstracts of Japan, unexamined applications, section C, vol. 4, No. 85, p. 149, Jun. 18, 1980, (Kokai No. 55-50891).

*Primary Examiner*—Lionel M. Shapiro
*Attorney, Agent, or Firm*—Fitzpatrick, Cella, Harper & Scinto

[57] ABSTRACT

The present invention provides a process for producing N-acetylneuraminate lyase using a microorganism constructed by recombinant DNA techniques.

6 Claims, No Drawings

PROCESS FOR PRODUCING N-ACETYLNEURAMINATE LYASE

BACKGROUND OF THE INVENTION

The present invention relates to a process for producing N-acetylneuraminate lyase (hereinafter referred to as "NA lyase") using a microorganism constructed by recombinant DNA techniques.

NA lyase (EC 4.1.3.3) is the enzyme which catalyzes the conversion reaction of N-acetylneuraminate into N-acetyl-D-mannosamine and pyruvate.

It is known that the enzyme is used for the determination of a substance containing sialic acid in serum for diagnostic purposes. It is also known that the enzyme exists in an animal tissue, pathogenic microorganisms such as *Clostridium perfringens, Vibrio cholerae*, etc. and various nonpathogenic microorganisms. Only a little amount of the enzyme is produced by culturing these microorganisms in a medium which is usually used in an enzyme production.

It has been reported that the yield of the enzyme was enhanced by adding N-acetylneuraminate to the medium (Japanese Patent Publication Nos. 54153/81 and 51751/81).

The utilization of N-acetylneuraminate is economically disadvantageous and it is demanded to develop the process for producing NA lyase without utilization of N-acetylneuraminate.

As a result of studies made to develop such a process, it has been found that an NA lyase producing microorganism constructed by incorporating a hybrid plasmid into a recipient of the genus *Escherichia* produces NA lyase in a high yield in a medium which does not contain N-acetylneuraminate.

SUMMARY OF THE INVENTION

In accordance with the present invention, NA lyase is produced by culturing a microorganism belonging to the genus *Escherichia* and having an ability to produce NA lyase and which is obtained by incorporating into a host strain of the genus *Escherichia* a hybrid plasmid wherein a DNA fragment with genetic information controlling NA lyase production which is derived from a donor strain is inserted.

DESCRIPTION OF THE INVENTION

As the DNA-donor strain used to construct the NA lyase producer of the present invention, any microorganism may be used so long as it belongs to the genus *Escherichia* and possesses genetic information controlling NA lyase production. Strains having a higher productivity of NA lyase are preferably used as the DNA-donor.

The DNA with genetic information controlling NA lyase production (hereinafter referred to as "chromosomal DNA") is extracted from the DNA donor in a well known manner, for example, phenol method described in Biochim. Biophys. Acta, Vol. 72, pp 619–629 (1963).

The thus obtained DNA is inserted into a vector DNA to prepare a hybrid DNA. The insertion of a chromosomal DNA into the vector DNA can be attained according to the usual manner.

The chromosomal DNA or the vector DNA is treated with a restriction endonuclease to prepare a chromosomal DNA fragment or a cleaved vector DNA and the mixture is treated with DNA ligase to obtain the hybrid DNA.

As the vector DNA, a conventional vector such as pBR322, ColEl, pSC101, pACYC177, pCRl, R6K or λ-phage, or their derivatives can be employed. Plasmid pBR322 is preferably used.

Examples of the restriction endonuclease are HindIII, BamHI, EcoRI, PstI and SalI, among which HindIII is preferable. As the DNA ligase, DNA ligase derived from $T_4$ phage may be preferably employed The hybrid DNA thus obtained can be incorporated into a microorganism of the genus *Escherichia* having no ability to produce NA lyase (hereinafter referred to as "NA lyase-non-producing strain") by conventional transformation techniques such as calcium ion treatment method described in J. Bacteriol., Vol. 119, pp 1072–1074 (1974)

The NA lyase-non-producing strain can be obtained by the following method. A wild strain of the genus *Escherichia* such as *Escherichia coli* C600 - SF8 is subjected to mutation treatment to obtain a mutant having no ability to utilize N-acetylneuraminate. The mutation is carried out by a conventional method, for example, treatment with mutagens such as N-methyl-N'-nitro-N-nitrosoguanidine.

The mutant having no ability to utilize N-acetylneuraminate can be obtained by culturing the microbial cells obtained by mutation treatment in a glucose minimal medium comprising 2 g/l glucose, 1 g/l $(NH_4)_2SO_4$, 7 g/l $K_2HPO_4$, 3 g/l $KH_2PO_4$, 0.1 g/l $MgSO_4.7H_2O$, 5 mg/l thiamine, 0.2 mM threonine, 0.2 mM leucine and 15 g/l agar. The formed colonies are replicated in the glucose minimal medium and N-acetylneuraminate minimal medium comprising 2 g/l N-acetylneuraminate, 1 g/l $(NH_4)_2SO_4$, 7 g/l $K_2HPO_4$, 3 g/l $KH_2PO_4$, 0.1 g/l $MgSO_4. 7H_2O$, 5 mg/l thiamine, 0.2 mM threonine, 0.2 mM leucine and 15 g/l agar. The colonies which can grow on the glucose minimal medium and cannot grow on the N-acetylneuraminate minimal medium are picked up to obtain NA lyase-non-producing strain. An example of such strain is *Escherichia coli* 0-2.

The screening method of the desired transformant is selected according to the kind of the restriction endonuclease used for preparing the hybrid DNA or the kind of the vector DNA utilized. When HindIII and plasmid pBR322 are used, the desired transformant is obtained by culturing the strain in the N-acetylneuraminate minimal medium containing ampicillin and picking up the formed colonies having NA lyase activity. An example of the microorganism containing the hybrid DNA is *Escherichia coli* H3 - 4 FERM BP-513.

The strain was deposited on March 24, 1984 with the Fermentation Research Institute, Agency of Industrial Science and Technology located at 1-3, Higashi 1 chome, Yatabe-machi, Tsukuba-gun, Ibaraki-ken 305, JAPAN under the Budapest Treaty.

The method for culturing the NA lyase producing strains thus obtained is conventional, and is similar to the known method for producing enzymes.

As the medium, either a synthetic or natural medium may be used so long as it contains an appropriate carbon source, nitrogen source and inorganic materials.

As the carbon source, carbohydrates such as glucose, sucrose, fructose, starch, starch hydrolyzate, molasses, etc. may be used in a concentration of 5–50 g/l.

As the nitrogen source, organic and inorganic ammonium salts such as ammonium sulfate, ammonium phosphate, ammonium carbonate, ammonium acetate, etc., nitrogen containing organic substances such as peptone, yeast extract, corn steep liquor and casein hydrolyzate, etc. may be used in a concentration of 5–20 g/l.

As the inorganic materials, potassium monohydrogen phosphate, potassium dihydrogen phosphate, magnesium sulfate, manganese sulfate, etc. may be used in a concentration of 0.05–5 g/l.

Culturing is carried out under aerobic conditions, for example, with shaking or stirring at a temperature of 25°–37° C. for 16–48 hours.

After completion of the culturing, the culture liquor is subjected to filtration, decantation, centrifugation, etc. to obtain microbial cells. The microbial cells are disrupted by appropriate means such as ultrasonic disintegration, grinding, etc. to obtain a cell extract and the extract is subjected to centrifugation to obtain a supernatant. Then the supernatant is subjected to conventional purification methods such as salting-out, dialysis, chromatography using ion exchange cellulose, Sephadex, gel filtration and the like to obtain the purified enzyme.

Certain specific embodiments of the invention are illustrated by the following representative examples.

EXAMPLE 1

(1) Preparation of chromosomal DNA harboring genetic information controlling NA lyase production

*Escherichia coli* KY 8482 was cultured in 300 ml of the medium (pH 7.2) comprising 1 g/l glucose, 10 g/l trypton, 5 g/l yeast extract and 5 g/l sodium chloride with shaking at 28° C. for 16 hours to obtain microbial cells.

The microbial cells were washed and treated with phenol by the method of Saito and Miura [Biochim. Biophys. Acta. 72, 619–629 (1963)], to obtain about 2 mg of a chromosomal DNA.

(2) Insertion of chromosomal DNA fragment into vector 2.6 µg of the chromosomal DNA obtained in step (1) was treated with restriction endonuclease HindIII at 37° C. for 2 hours to cleave the DNA chains and then heated at 65° C. for 10 minutes. 2.6 µg of vector DNA, pBR322 (product of Bethesda Research Laboratories, Co.) was treated with restriction endonuclease HindIII at 37° C. for 2 hours to cleave the DNA chains and then heated at 65° C. for 10 minutes.

The digested chromosomal DNA solution and cleaved vector DNA solution were mixed and subjected to the ligation reaction of DNA fragments with T4 phage DNA ligase at 4° C. for 16 hours. The reaction mixture was heated at 65° C. for 10 minutes to obtain a hybrid DNA solution.

(3) Genetic transformation with the hybrid plasmid harboring the genetic information controlling NA lyase production NA lyase-non-producing strain *Escherichia coli* 0-2 which was derived from *Escherichia coli* C600 - SF8 by mutation treatment was cultured in 40 ml of L-medium at 37° C. with shaking. Cells in exponential growth phase ($OD_{660}$=about 0.40) were harvested and washed with 0.1M $CaCl_2$ solution. Then, the cells were suspended in 1 ml of 0.1M $CaCl_2$ solution.

The DNA obtained in step (2) was added to 0.15 ml of the suspension. After incubating at 0° C. for 30 minutes, the suspension was heated at 37° C. for 20 minutes to incorporate the DNA into the cells. The cells were inoculated into 1.5 ml of L-medium and cultured at 37° C. for 2 hours with shaking. The cultured cells were harvested and washed.

The resultant cells were spread on an agar plate of N-acetylneuraminate minimal medium comprising 2 g/l N-acetylneuraminate, 1 g/l $(NH_4)_2SO_4$, 7 g/l $K_2HPO_4$, 3 g/l $KH_2PO_4$, 0.1 g/l $MgSO_4 \cdot 7H_2O$, 5 µg/ml thiamine, 0.2 mM threonine, 0.2 mM leucine and 15 g/l agar (pH was adjusted to 7.0) and containing 20 µg/ml ampicillin. The plate was incubated at 30° C. for 2 days. Colonies formed on the plate were picked up and examined for NA lyase activity to obtain H3 - 4 strain as NA lyase-producing transformant.

EXAMPLE 2

Strains indicated in Table 1 were inoculated in L-medium and in L-medium containing 1 g/l N-acetylneuraminate and were cultured at 30° C. with shaking for 18 hours. After completion of the culturing, the culture liquor was subjected to centrifugation to obtain microbial cells which were then washed with physiological saline solution. The microbial cells were subjected to ultrasonic disintegration to obtain an extract. The NA lyase activity of the extract is shown in Table 1.

The transformant strain H3 - 4 produced NA lyase using a medium which does not contain N-acetylneuraminate.

TABLE 1

| Strain | Induction* | Yield of NA lyase (U/ml) |
|---|---|---|
| *Escherichia coli* K-12 C600 | + | 0.238 |
| | − | 0.012 |
| *Escherichia coli* KY 8482 | + | 0.277 |
| | − | 0.010 |
| *Escherichia coli* H3 - 4 | + | 0.324 |
| | − | 0.190 |

*+: L-medium + N—acetylneuraminate (1 g/l)
−: L-medium

EXAMPLE 3

H3 - 4 strain was inoculated in 300 ml of the medium (pH 7.0) comprising 1 g/l glucose, 10 g/l trypton, 5 g/l yeast extract, 5 g/l sodium chloride and 20 µg/ml ampicillin in a 2 l-Erlenmeyer flask and cultured at 30° C. with shaking for 18 hours. The culture liquor was subjected to centrifugation to obtain microbial cells. The microbial cells were suspended in 20 ml of 0.01M phosphate buffer (pH 7.0) and the suspension was subjected to ultrasonic disintegration to disrupt the cells and extract the enzyme.

To the extract was added ammonium sulfate and the precipitates which were deposited by the saturation with 30–80% ammonium sulfate were recovered.

The precipitates were dissolved in 5 ml of 0.01M phosphate buffer (pH 7.0) and the solution was subjected to dialysis with 1 l of the same buffer solution for 24 hours. The dialysate was passed through a column (Volume: 250 ml, Diameter: 2.5 cm) packed with DEAE-Sephadex equilibrated with the same buffer solution, whereby NA lyase was adsorbed on the DEAE-Sephadex.

The column was washed with the same phosphate buffer to remove contaminant proteins. Concentration gradient elution was carried out with the same phosphate buffer (pH 7.0) and the same phosphate buffer containing 1.0M NaCl.

The active fractions were combined and the precipitates which were deposited with a saturated solution of 90% ammonium sulfate were recovered by centrifugation (12,000 xg, 20 minutes) and were dissolved in 5 ml of 0.01M phosphate buffer (pH 7.0).

The solution was subjected to dialysis with 1 l of the same buffer (pH 7.0) for 24 hours.

The dialysate was subjected to freeze-drying to obtain 20 mg of purified NA lyase powder preparation (specific activity 3.0 unit/mg).

What is claimed is:

1. A process for producing N-acetylneuraminate lyase which comprises culturing a microorganism of the genus Escherichia which is capable of producing N-acetylneuraminate lyase in the absence of an N-acetylneuraminate lyase-inducing compound in a culture medium, said culture medium devoid of N-acetylneuraminate lyase-inducing compounds and recovering N-acetylneuraminate lyase accumulated in the culture liquor.

2. The method according to claim 1, wherein said microorganism is obtained by incorporating into a host strain of the genus Escherichia a hybrid vector within which a DNA fragment is inserted, said DNA fragment having genetic information controlling N-acetylneuraminate lyase production derived from a donor strain of the genus Escherichia.

3. The method according to claim 1, wherein said microorganism belongs to the species *Escherichia coli*.

4. The method according to claim 3, wherein said microorganism is *Escherichia coli* FERM BP-513.

5. The method according to claim 2, wherein said hybrid vector is derived from a member selected from the group consisting of ColE1, pSC101, pBR322, pACYC177, pCR1, R6K and λphage.

6. A biologically pure culture of a microorganism having the identifying characteristics of *Escherichia coli* FERM BP-513.

* * * * *